(12) United States Patent
Shargian

(10) Patent No.: US 12,257,382 B1
(45) Date of Patent: *Mar. 25, 2025

(54) MOUTHPIECE WITH FLAVORED ATTACHMENT

(71) Applicant: BSD SAGI, LLC, New Orleans, LA (US)

(72) Inventor: Moshe Shargian, Metairie, LA (US)

(73) Assignee: BSD SAGI, LLC, New Orleans, LA (US)

( * ) Notice: Subject to any disclaimer, the term of this patent is extended or adjusted under 35 U.S.C. 154(b) by 163 days.

This patent is subject to a terminal disclaimer.

(21) Appl. No.: 18/131,165

(22) Filed: Apr. 5, 2023

Related U.S. Application Data

(63) Continuation of application No. 16/991,677, filed on Aug. 12, 2020, now Pat. No. 11,779,714.

(60) Provisional application No. 63/062,706, filed on Aug. 7, 2020, provisional application No. 62/885,573, filed on Aug. 12, 2019.

(51) Int. Cl.
*A61M 15/00* (2006.01)

(52) U.S. Cl.
CPC .... *A61M 15/0026* (2014.02); *A61M 15/0086* (2013.01); *A61M 15/009* (2013.01); *A61M 2240/00* (2013.01)

(58) Field of Classification Search
CPC ........ A61M 11/00–08; A61M 15/0026; A61M 15/0086; A61M 15/009; A61M 2240/00; B05B 17/00–085
USPC .................................................... 128/200.23
See application file for complete search history.

(56) References Cited

U.S. PATENT DOCUMENTS

| | | | |
|---|---|---|---|
| 2005/0061318 A1* | 3/2005 | Faram | A61M 16/0096 128/204.21 |
| 2014/0166029 A1* | 6/2014 | Weigensberg | A24F 40/30 131/329 |
| 2019/0111223 A1* | 4/2019 | Harrison | A61M 11/06 |

FOREIGN PATENT DOCUMENTS

WO    WO-2004096110 A2 * 11/2004  ............. A63B 23/18

* cited by examiner

*Primary Examiner* — Elliot S Ruddie
(74) *Attorney, Agent, or Firm* — AdamsIP, LLC

(57) ABSTRACT

A mouthpiece with a flavored attachment is provided. The flavored attachment fits into a recess on an exterior of the mouthpiece and has projecting portions that extend outward from the attachment. The mouthpiece has a guard that retains the flavored attachment in place. The guard has openings that allow the projecting portions of the flavored attachment to extend through the openings of the guard so that the user tastes the flavored attachment when the user holds the mouthpiece in the user's mouth.

20 Claims, 22 Drawing Sheets

MOUTHPIECE WITH FLAVORED ATTACHMENT

CROSS-REFERENCE TO RELATED APPLICATIONS

This application is a continuation of U.S. application Ser. No. 16/991,677, filed on Aug. 12, 2020, which claims the benefit of U.S. Provisional Application No. 63/062,706, filed on Aug. 7, 2020, and U.S. Provisional Application No. 62/885,573, filed on Aug. 12, 2019, which applications are incorporated herein by reference.

BACKGROUND

1. Field of the Disclosure

The present disclosure relates to pediatric inhalers used for respiration therapy wherein the patient inhales tiny droplets of a doctor prescribed pharmaceutical atomized by a compressor, tube and nebulizer that contains the prescribed pharmaceutical. More particularly, the present disclosure relates to a method and apparatus designed to increase the efficacy of pediatric inhalers that are designed for use with pharmaceuticals added to a reservoir of the inhaler by providing a candy or flavored (e.g., consumable) attachment which can be adhered to the mouthpiece of a pediatric inhaler so that the child will utilize the mouthpiece for the requisite time (e.g., as much as 15-20 minutes) to ensure proper dosage. Accordingly, the flavored attachment is designed to last long enough for the required dosage to be inhaled or consumed. In another embodiment, the present inhaler can comprise an inhaler wherein the mouthpiece is provided with the candy attachment in a single unit.

2. Related Information

Pediatric inhaler devices are known and commercially available (e.g., Vios® from Pari Respiratory Equipment, Inc. (www.pari.com) of Midlothian, VA). Such pediatric inhaler devices provide a mouthpiece for the child to hold in his or her mouth, tubing to connect to a machine that has a compressor, a nebulizer or nebulizer cup having a chamber defining a reservoir for holding a selected pharmaceutical (e.g., Albuterol or budesonide), an air inlet connector providing an interface between the tubing and the nebulizer, and a connector that interfaces the nebulizer and mouthpiece (e.g., a fitting such as a tee fitting).

The following U.S. Patents are incorporated herein by reference: U.S. Pat. Nos. 6,702,997; 8,671,934; 9,452,270; and 9,452,274; U.S. Patent Application Publication Nos.: 2009/0062855; 2012/0190999; 2014/0202457; 2014/0207016; 2014/0261400; 2018/0192693; and 2019/0111223; and International Patent Publication No. WO 2017007489.

SUMMARY

The apparatus of the present disclosure is an inhaler attachment for an inhaled pharmaceutical for patients, especially children, which has candy or a flavored, consumable coating on the mouthpiece (or, alternatively, a strip of candy or flavored, consumable coating with an adhesive that can be applied to the mouthpiece of the inhaler). The candy should preferably last long enough to ensure that the child will keep the mouthpiece in his or her mouth long enough for a proper dose of medicine to be consumed (for example, at least about 15 minutes), but can last between 1 and 15 minutes, and up to 15 minutes (or even longer if the proper dosage requires more time). The duration that the candy or flavored, consumable coating can last can vary depending on the dosage time required. The attachment of candy on the mouthpiece will aid in solving the problem often encountered when children are reluctant to take medicine or consume the full amount of medicine needed through a mouthpiece that is part of a nebulizer or nebulizer cup connected to an air compressor.

The present device comprises a candy adhesive or the like, such as a flavored, consumable coating which can be applied to the mouthpiece of an inhaler or on a nebulizer or on similar medical aeration therapy devices. Preferably, the present device can be used on mouthpieces for nebulizers, chambers, spacers, puffers, masks, inhalers, respiratory devices, and respiratory tubing, such as those used in hospital settings. Preferably, the device can be made in different sizes for different age children. For example, there may be small, medium, or large sizes available, or some other suitable size scale. In tests, gummy bear type candy and Nutella have been used. The apparatus comprises a candy and can be different types of materials, such as hard candy, jelly candy, frozen candy, dissolvable candy (such as that used in LISTERINE® strips), or other suitable candy material. The apparatus can comprise a separate adhesive layer which is utilized to adhere the candy to the mouthpiece of an inhaler, for example. The candy may be adhered to the inhaler where the mouthpiece is located. A preferred embodiment of the present device comprises an edible adhesive layer. In certain embodiments, the adhesive layer can be part of, and the same material as, candy. The adhesive can be included in the candy or even added to it later. Various candies or flavors can be utilized. The candy layer can be of various thicknesses depending on the desired length of treatment. The apparatus of the present disclosure can be provided as an attachment to attach to an inhaler, or as part of the inhaler in a single device.

The apparatus can comprise a candy surrounding a sleeve which can then be placed onto an inhaler. The sleeve can be sold already assembled on the inhaler. The sleeve can be made of elastic material, for example. An advantage of the embodiments which comprise the sleeve is that it can easily be attached and detached from a mouthpiece.

The present device presents a candy attachment for a mouthpiece which is used to distribute medicine to a patient as part of aeration therapy. In one embodiment, the candy is able to slip into the inhaler tube, wherein the air flow with the medicine travels through the candy. Similarly, the candy acts as an inhaler tube and is connected into the inhaler and the air flow is able to flow out of the candy.

In another embodiment and related embodiments, the candy or similar flavored substance is locked onto the outside of the nebulizer using a locking device (e.g., silicone), and the candy or similar flavored substance is shaped such that it can be locked in place using the locking device, but consumed by the child while the child receives treatment via the nebulizer/inhaler. Other variations could include a lollipop shaped candy with a locking mechanism for the lollipop handle.

In one embodiment, there is a safety net or guard on each candy to prevent swallowing or aspiration by the patient. The safety net can be placed on the device to cover and protect the user, but it is preferably on each candy piece in embodiments where the candy is separate from the device. The safety net can be mesh and made of silicone, plastic, or other suitable material. In some embodiments, the safety net is also made of candy or food substance. Alternatively, there could be a slide mechanism similar to a pod container on a dishwasher, wherein the safety net surrounds the candy and is anchored by a rail sliding to the device.

Preferably, the candy is available in various shapes, such as bumps, stripes, spikes or other suitable shapes, some of which are shown in the figures. These shapes can also include cartoon characters, animals, logos, or other desirable designs (not shown). Additionally, the candy can be in a sponge-type shape and form that allows the treat to be absorbed in different levels of liquid types and concentrations. In some embodiments, there are provided different control mechanisms for treatment level, duration and timing, for example, a button, spring, speed stick, injection, or other suitable mechanism.

In another embodiment, molds are provided to enable a patient to make their own candy shapes for home medicine applications.

The present device may also include flavor strips that can be wrapped around the device.

The mouthpiece of the present disclosure is preferably a universal size which can fit on any inhaler; alternatively, it can be provided in sufficient sizes to fit on any commercially available inhaler. For example, the dimensions can be as follows: ID—1-3.5 cm, preferably 1.5-2.5 cm, most preferably 2-2.5 cm; OD—1.5-3.8 cm, preferably 1.7-2.8 cm, most preferably 2-2.7 cm; length-5-15 cm, preferably 6.5-12.5 cm, most preferably 6.5-10.5 cm.

The flavorings of the candy (or other flavored substance on/in the mouthpiece) can be any appropriate flavoring, such as disclosed in US Patent Publication No. US 2007/0031343 A1, incorporated herein by reference. Also, one could flavor the medicine of the inhalant as disclosed in US Patent Publication No. US 2007/0031343 A1.

The foregoing summary has outlined some features of the system and method of the present disclosure so that those skilled in the pertinent art may better understand the detailed description that follows. Additional features that form the subject of the claims will be described hereinafter. Those skilled in the pertinent art should appreciate that they can readily utilize these features for designing or modifying other structures for carrying out the same purpose of the system and method disclosed herein. Those skilled in the pertinent art should also realize that such equivalent designs or modifications do not depart from the scope of the system and method of the present disclosure.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION

In the Summary above and in this Detailed Description, and the claims below, and in the accompanying drawings, reference is made to particular features, including method steps, of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with/or in the context of other particular aspects of the embodiments of the invention, and in the invention generally.

The term "comprises" and grammatical equivalents thereof are used herein to mean that other components, steps, etc. are optionally present. For example, a system "comprising" components A, B, and C can contain only components A, B, and C, or can contain not only components A, B, and C, but also one or more other components. As used herein, the term "created vector" and grammatical equivalents refers to the one or more vectors created by the processor based on the mapped activation levels of the one or more sensors.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The invention now will be described more fully hereinafter with reference to the accompanying drawings. This invention may, however, be embodied in many different forms and should not be construed as limited to the embodiments set forth herein. Rather, these embodiments are provided so that this disclosure will be thorough and complete, and will fully convey the scope of the invention to those skilled in the art. One skilled in the art may be able to use the various embodiments of the invention.

Figure 1:
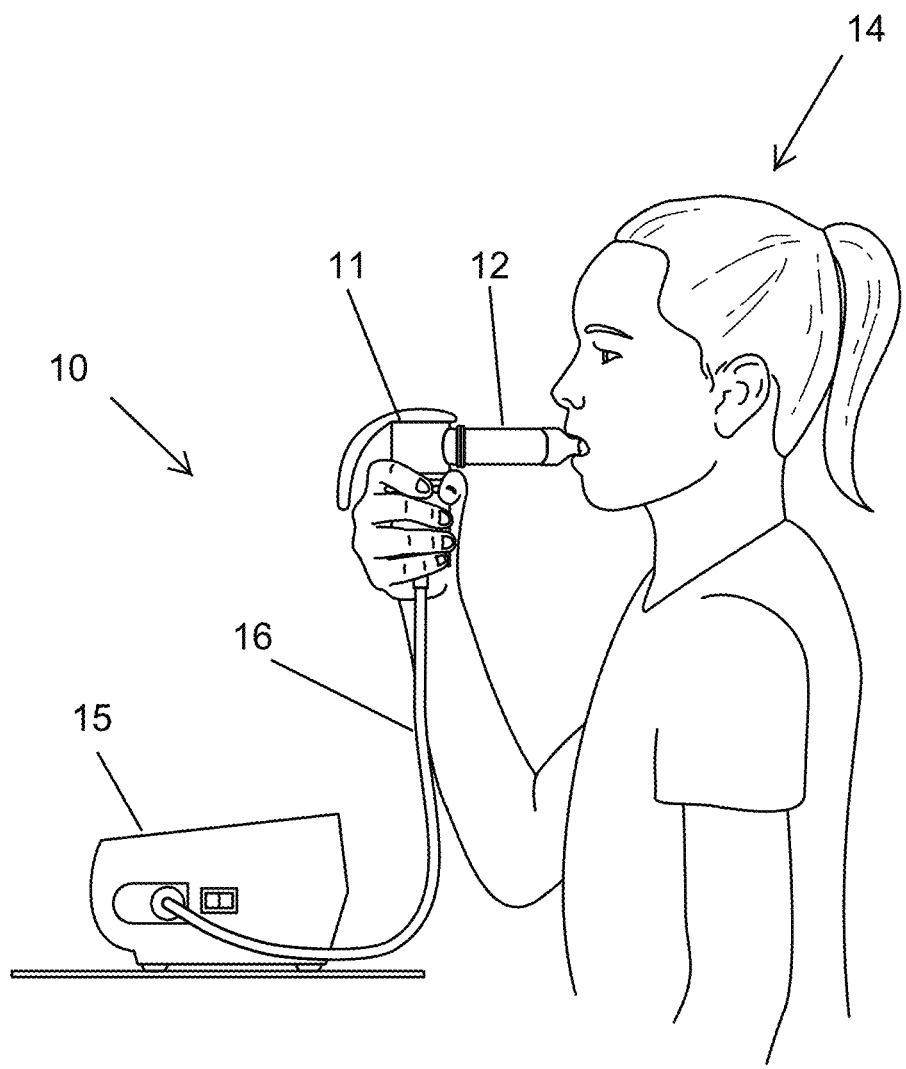
FIG. 1 is a perspective view of a preferred embodiment of the apparatus of the present disclosure.

FIG. 1 is a schematic diagram of a pediatric inhaler 10 in one embodiment of the method and apparatus of the present disclosure wherein a nebulizer or nebulizer cup 11 having a mouthpiece 12 is fitted with a candy item, layer, coating or candy fitment 13 (see FIGS. 2-3, 5-7, 11, 14 and 24-26) that provides flavor to a child 14. Nebulizer cup 11 is provided with air from compressor 15 and tubing section 16. A nebulizer cup with a mouthpiece tubing section and compressor is commercially available and sold under the trademark Vios and from Pari Respiratory Equipment, Inc. of Midlothian, VA. The nebulizer cup 11 turns a liquid medicine component contained in a reservoir or medicine container (not shown) into an aerosol mist. For respiration or aerosol therapy, repeated inhaling/exhaling is required while simultaneously holding the mouthpiece in a user's mouth and while the user's lips seal against the mouthpiece. For very young users, children or toddlers concentration can be low so that the user does not continuously inhale/exhale for a doctor prescribed time interval that can be about 5-15 minutes or more. The pharmaceutical in the reservoir or container can be albuterol, budesonide or other drug that is doctor prescribed for respiratory or aerosol therapy used to treat patients having asthma, pneumonia, bronchitis, bronchiolitis, chronic obstructive pulmonary disease (COPD), and any other condition affecting air flow in the lungs.

Figure 18:
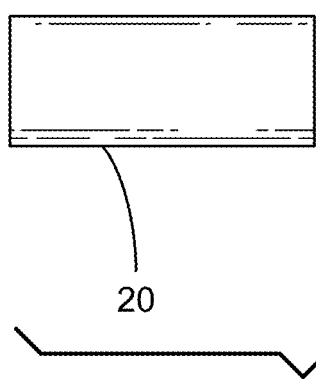
FIG. 18 is an exploded side view of a preferred embodiment of the apparatus of the present disclosure.
Figure 19:
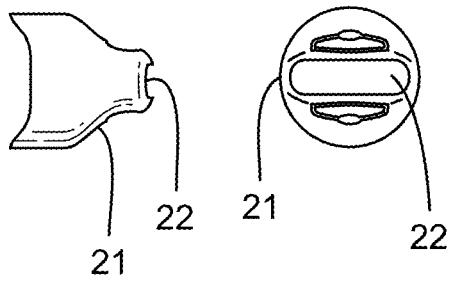
FIG. 19 is a fragmentary end view of a preferred embodiment of the apparatus of the present disclosure.
Figure 20:
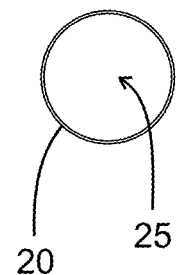
FIG. 20 is a fragmentary end view of a preferred embodiment of the apparatus of the present disclosure.
Figure 21:
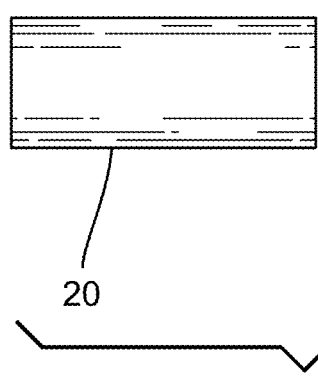
FIG. 21 is an exploded side view of a preferred embodiment of the apparatus of the present disclosure.
Figure 22:
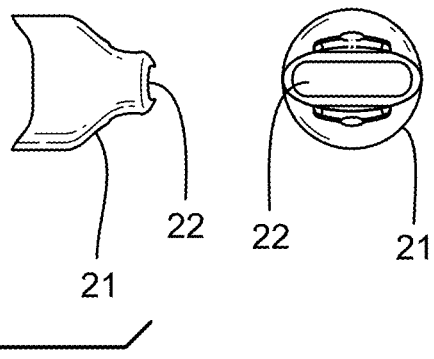
FIG. 22 is a fragmentary end view of a preferred embodiment of the apparatus of the present disclosure.
Figure 23:
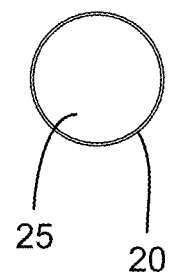
FIG. 23 is a fragmentary end view of the preferred embodiment of the apparatus of the present disclosure.
Figure 24:
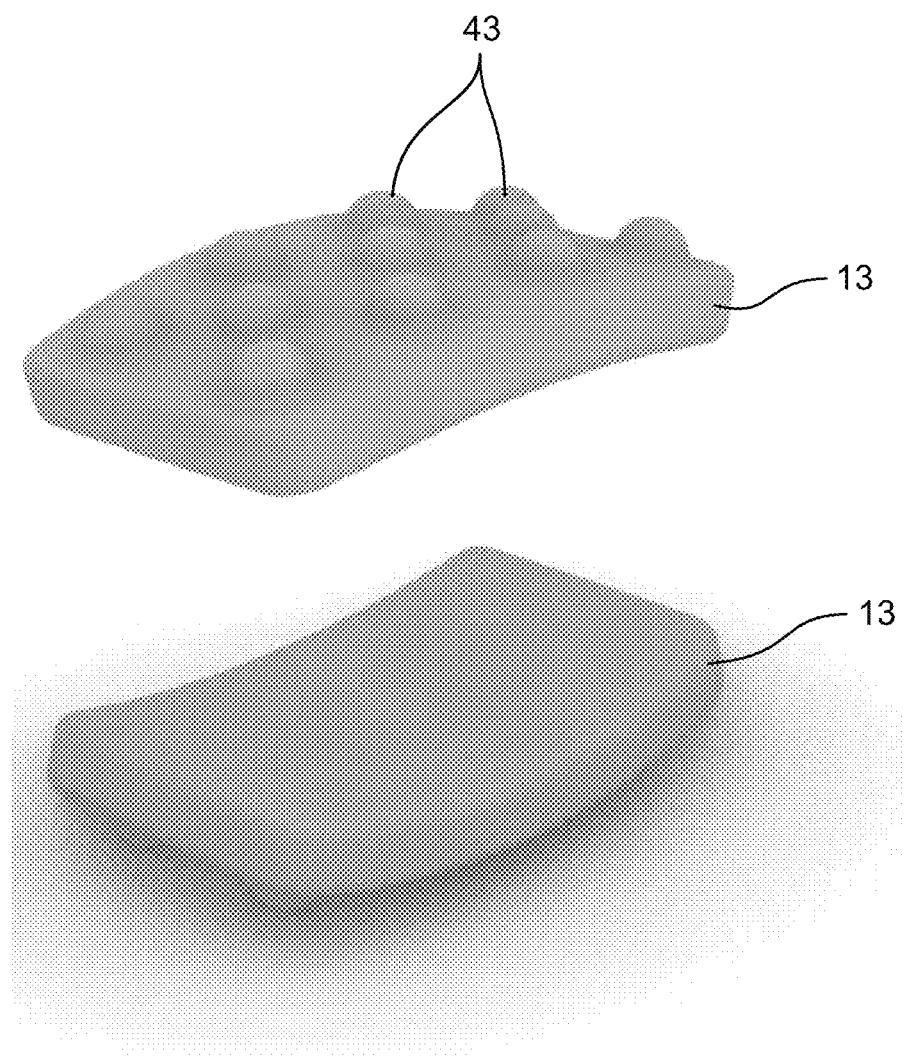
FIG. 24 is a fragmentary perspective view of a preferred embodiment of the apparatus of the present disclosure showing the candy inserts.
Figure 25:
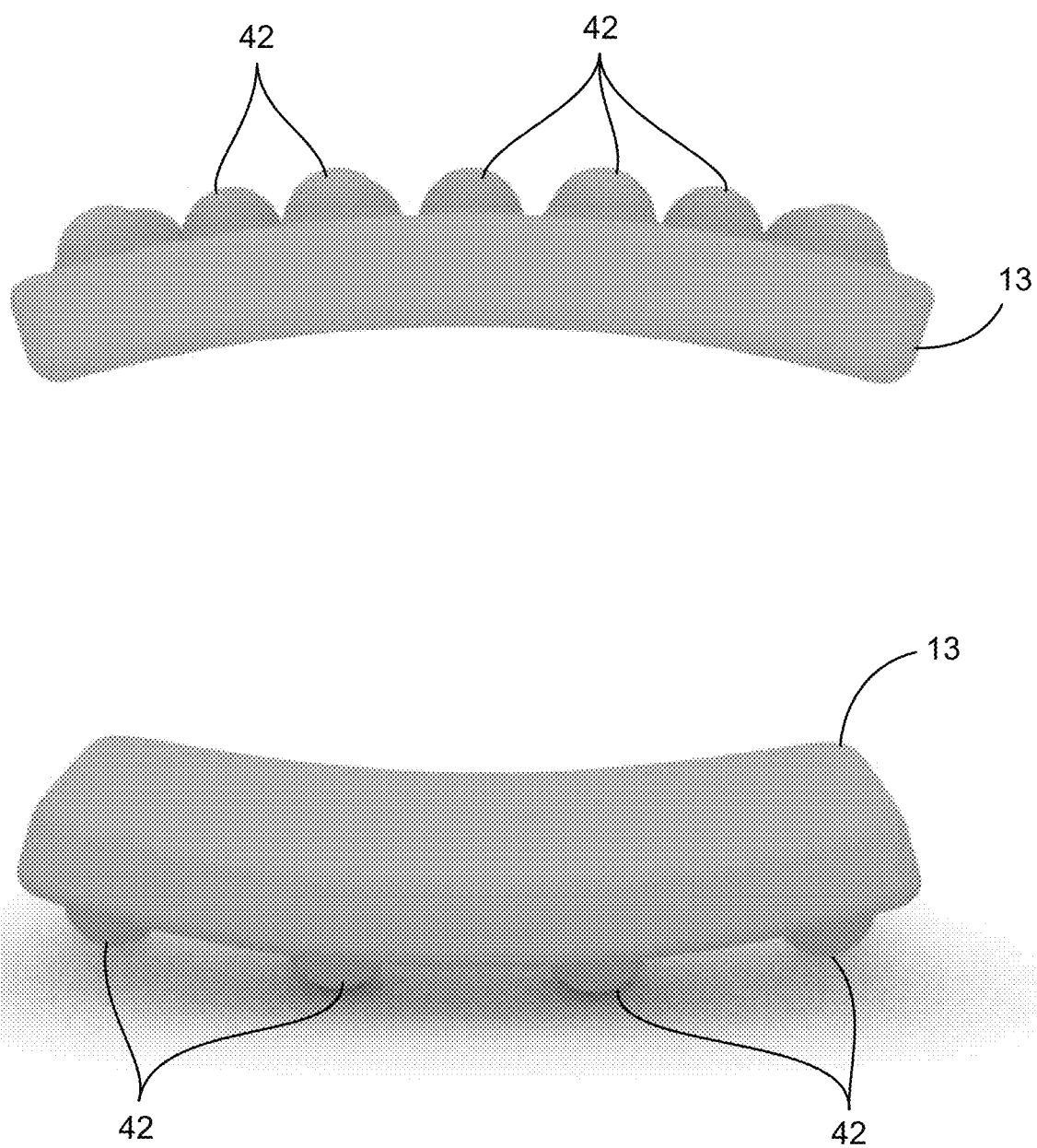
FIG. 25 is a fragmentary side view of a preferred embodiment of the apparatus of the present disclosure showing the candy inserts.
Figure 26:
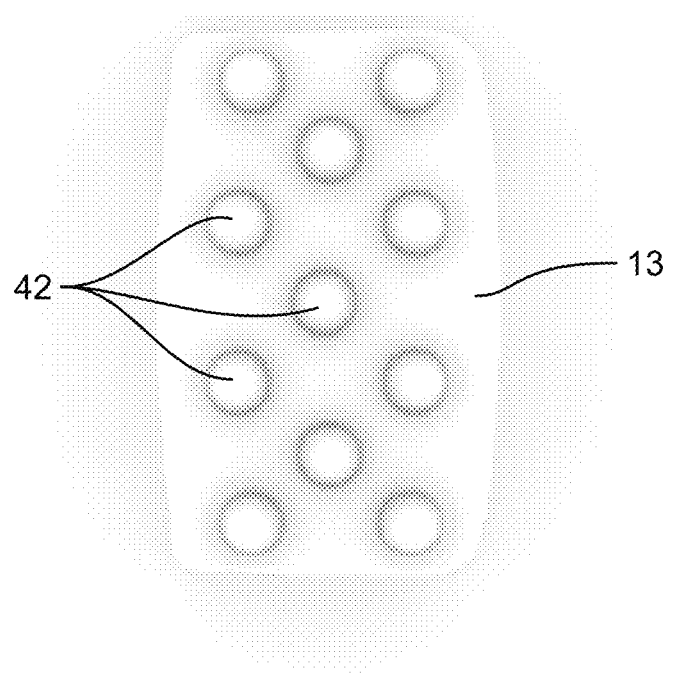
FIG. 26 is a fragmentary top view of a preferred embodiment of the apparatus of the present disclosure showing the candy insert.

FIGS. 2-17 show specially configured mouthpiece having mouthpiece body 20 having end portion 21 with opening 22 and end portion 23 having opening 24. An open-ended bore 25 connects opening 22 with opening 24. End portion 23 can connect with a nebulizer or nebulizer cup 11 (see FIG. 11). Body 20 can be a two-part body as seen in FIG. 18. Alternatively, body 20 and its components (including guard assemblies 26, 27, and candy inserts 13) can be a part of a nebulizer or nebulizer cup 11.

Figure 4:
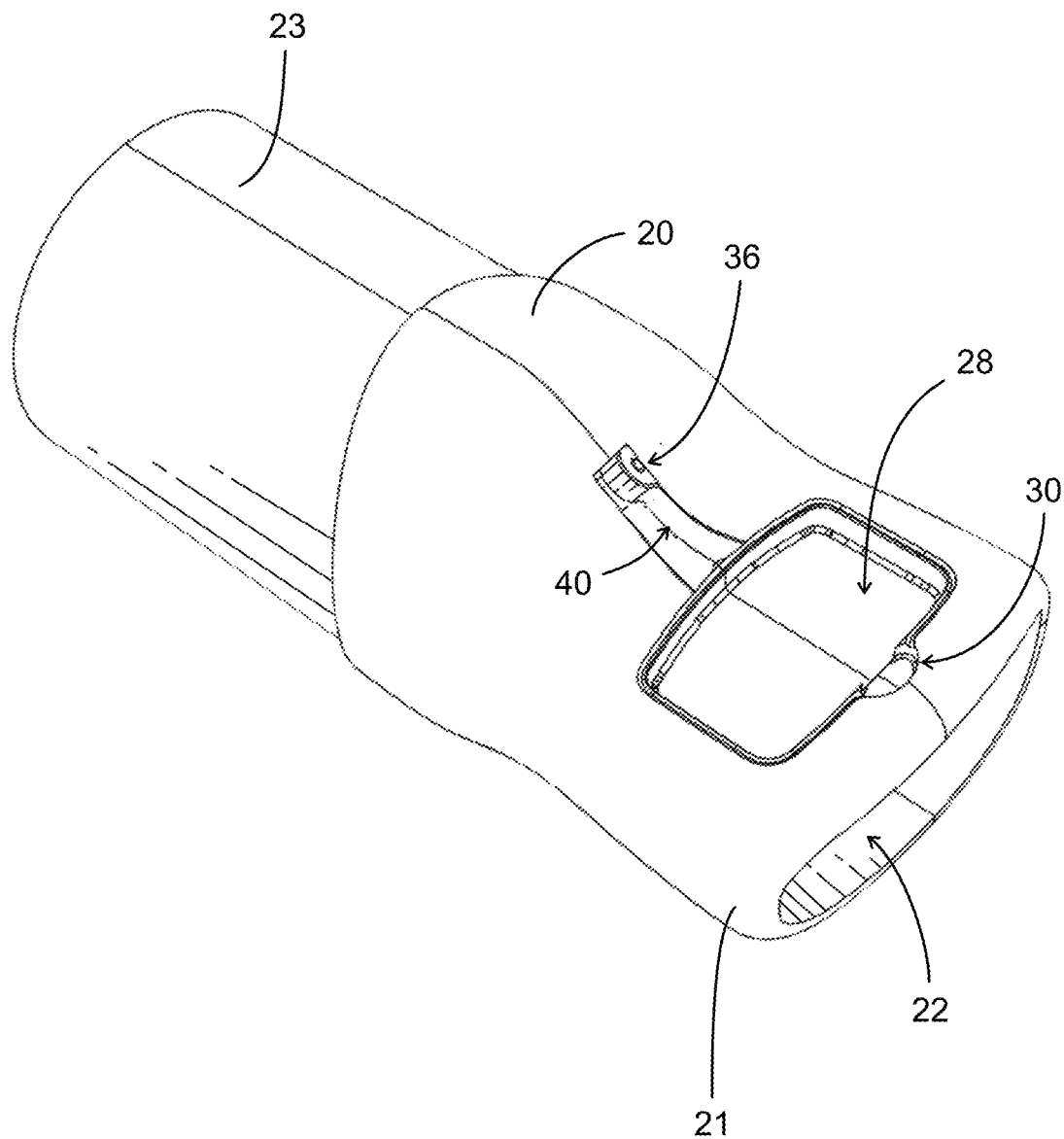
FIG. 4 is a perspective view of a preferred embodiment of the apparatus of the present disclosure with guard and candy insert removed.
Figure 13:
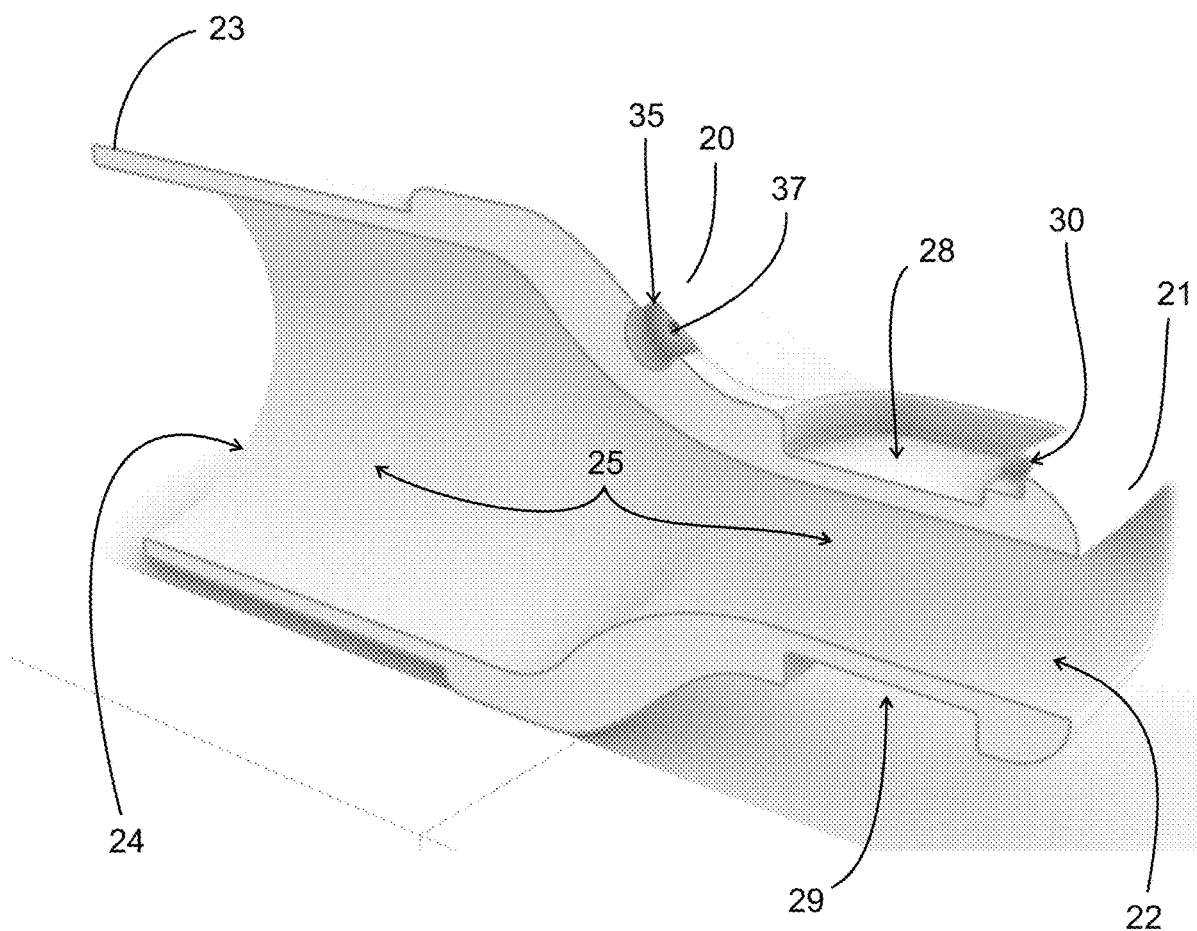
FIG. 13 is a partial sectional perspective view of a preferred embodiment of the apparatus of the present disclosure with candy insert removed.
Figure 14:
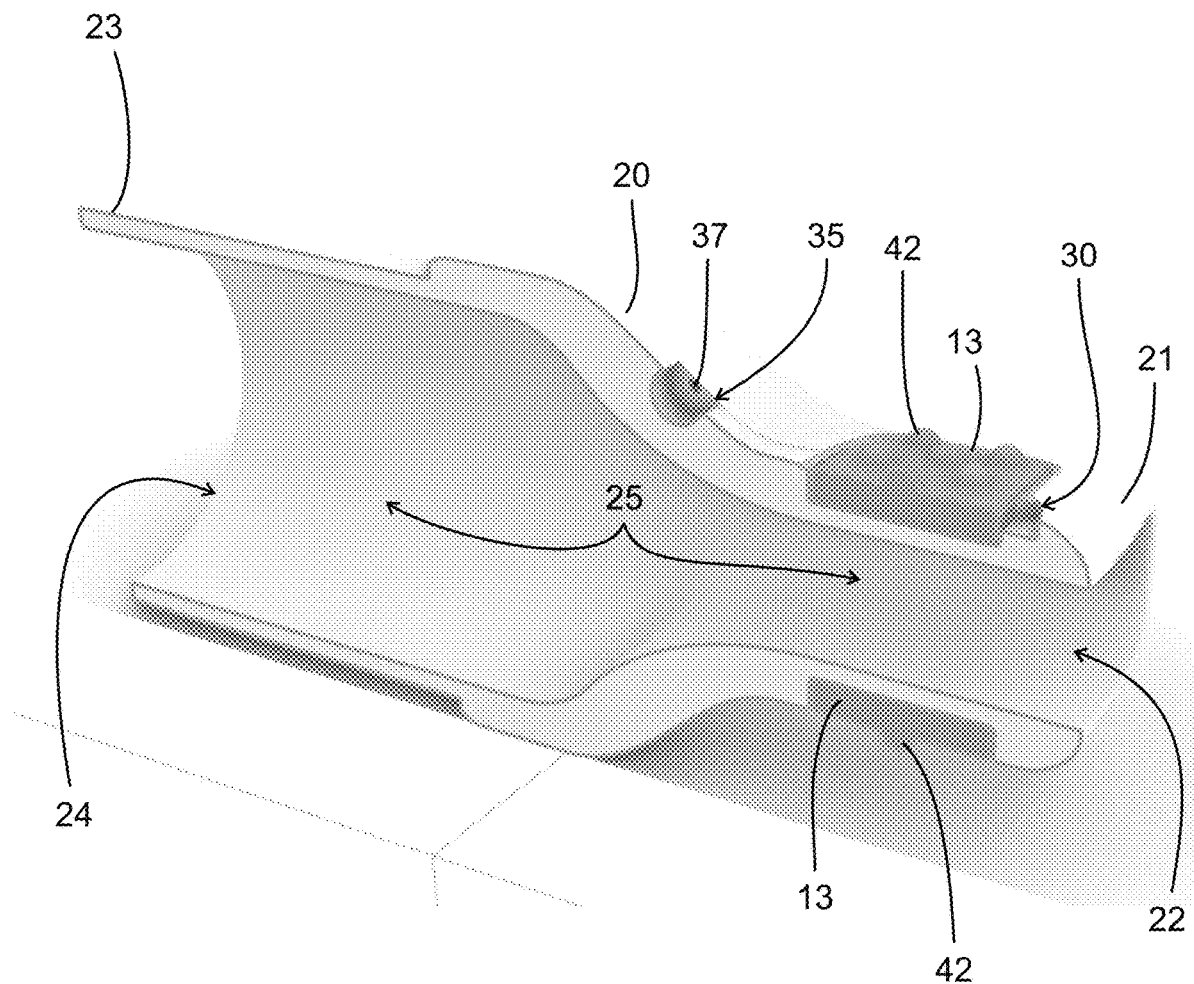
FIG. 14 is a partial sectional perspective view of a preferred embodiment of the apparatus of the present disclosure with guard removed.
Figure 15:
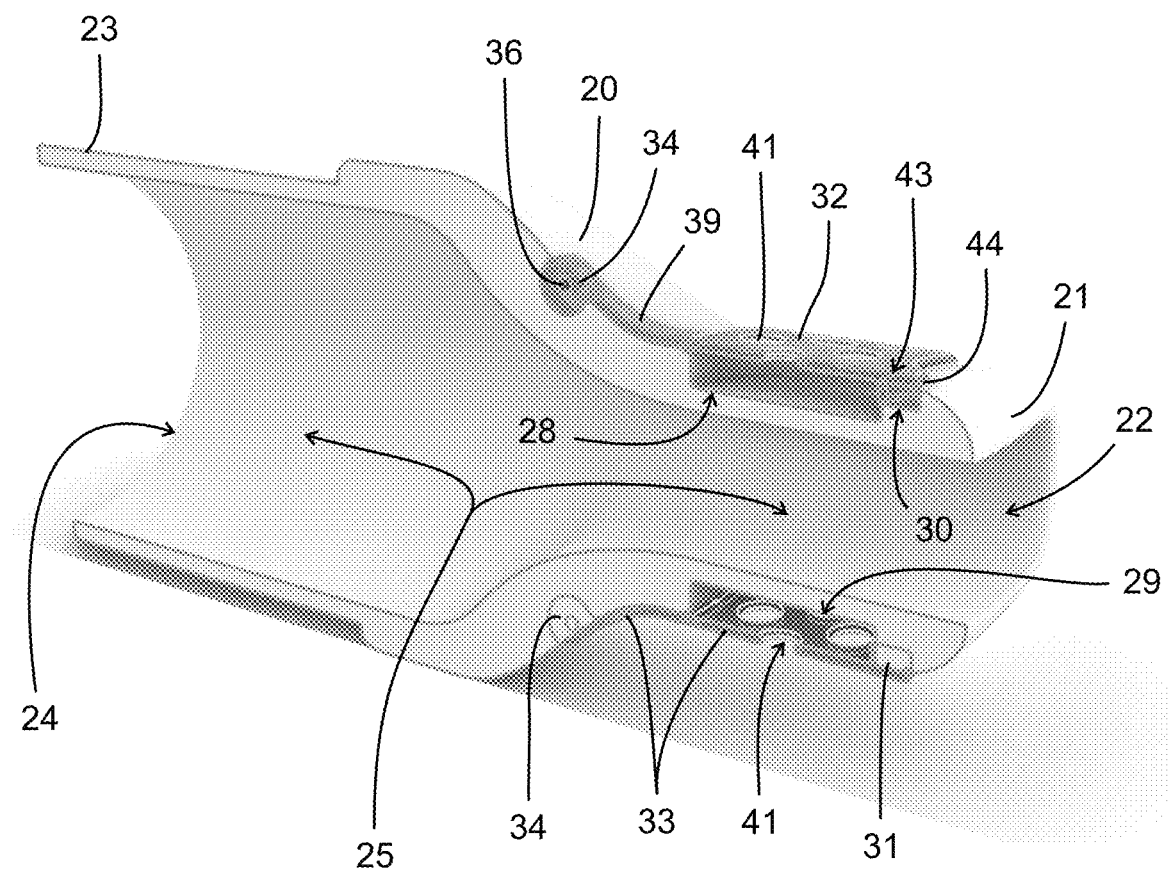
FIG. 15 is a partial sectional perspective view of a preferred embodiment of the apparatus of the present disclosure with candy insert removed and guards in closed position.
Figure 16:
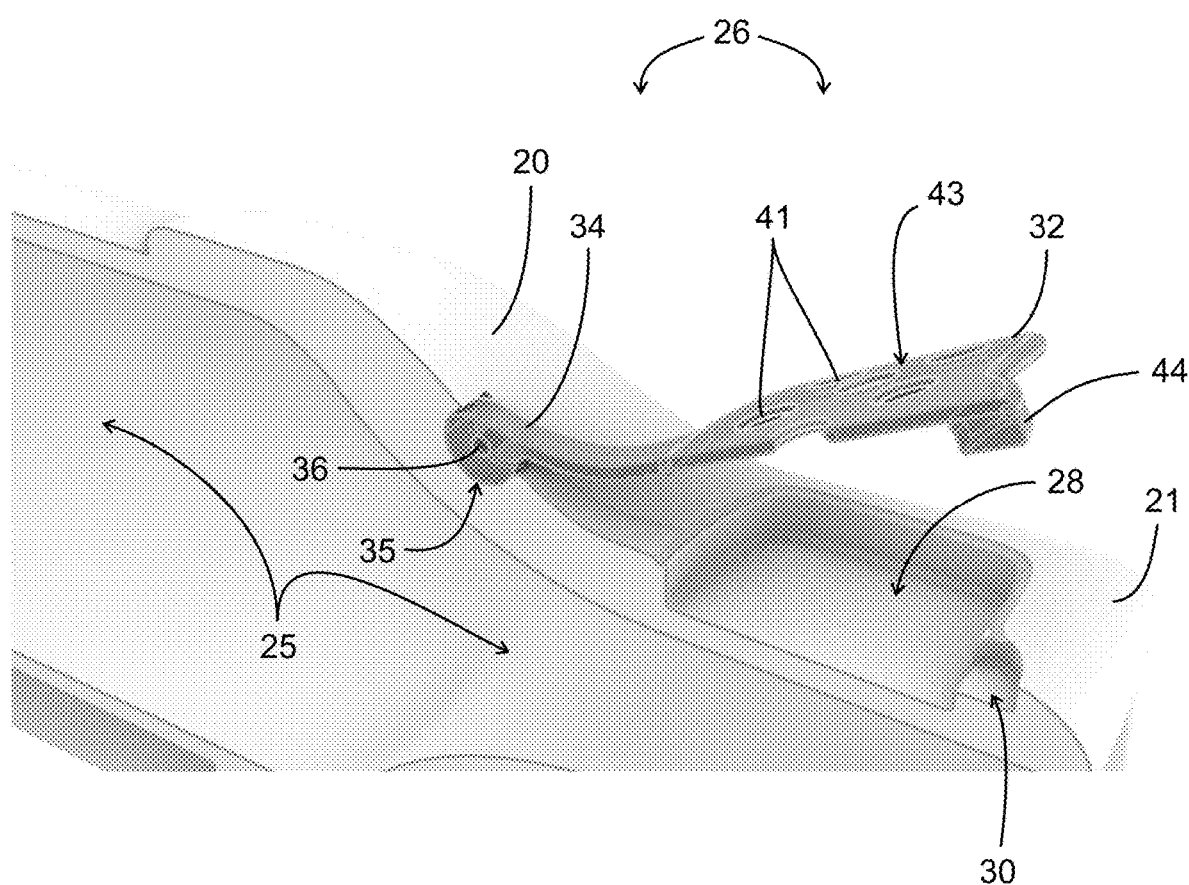
FIG. 16 is a perspective view of a preferred embodiment of the apparatus of the present disclosure with candy insert removed and guards in open position.
Figure 17:
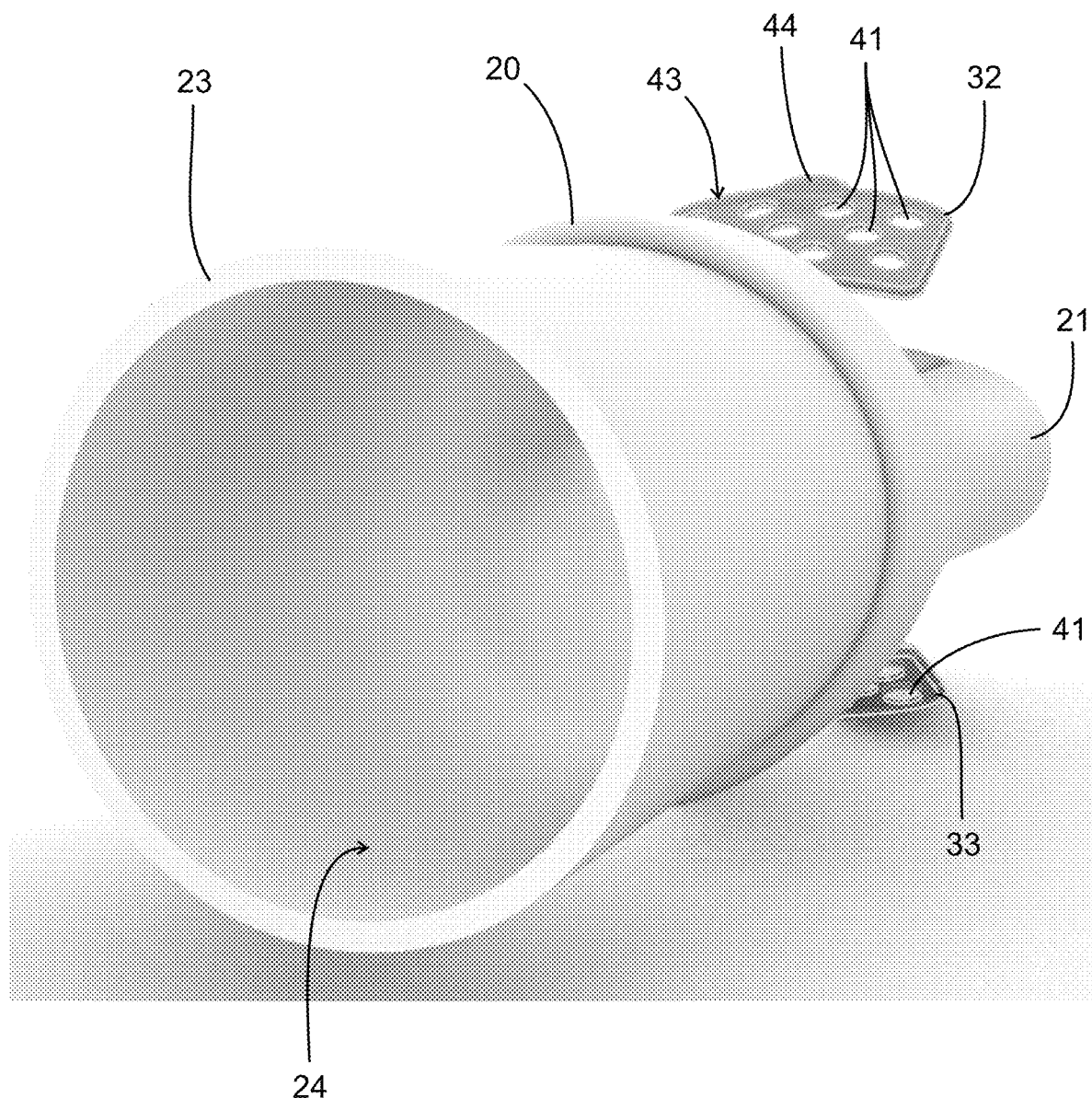
FIG. 17 is a perspective view of a preferred embodiment of the apparatus of the present disclosure with candy insert removed and guards in open position.

In FIGS. 4 and 13, body 20 has upper 28 and lower 29 recesses (e.g., rectangular or polygonal shape) each receptive of a candy insert 13. An arcuate or semicircular recess is provided next to each polygonal or rectangular recess 28, 29. Semicircular or arcuate recess 30 is next to recess 28. Semicircular or arcuate recess 31 is next to recess 29. Recesses 28, 29 can be of the same size and shape. Recesses 30, 31 can be of the same size and shape.

Each candy insert 13 fits into a recess 28 or 29 as seen in FIGS. 2, 3, 6, 7, 11 and 14. Upper and lower guards assemblies or safety nets 26, 27 are provided to prevent inadvertent removal of a candy insert 13 during use. These guard assemblies include upper candy holding guard 32 and lower candy holding guard 33 as seen in FIGS. 2, 5-8, 10, 11 and 15-17. Each guard assembly 26, 27 includes a hinge portion 34 that connects to body 20 at a hinge recess 36 via pin, pinned connection or pivot pin 36. Pin openings 37 in body 20 hold end portions of pin 36.

Each guard 32, 33 includes a rectangular portion 38 that is connected to hinge portion 34 with strap or arm 39. A recess 40 in body 20 is receptive of strap or arm 39. Rectangular portion 38 has openings 41 that are receptive of projections or bumps 42 on each insert 13 that project away from each candy insert 13 and away from body 20 as seen in FIGS. 2, 3, 5, 6, 7 and 11. Notice in FIGS. 2, 5 and 11 that the bumps or projections 42 extend above the outer surface 43 of each candy guard 32, 33. Preferably, these projections 42 extend approximately 2-3 mm above the base of the flavor attachment 13.

When a child user puts his or her mouth on end portion 21 of body 20, he or she will be able to taste the candy insert 13 projections 42. The bumps or projections can be sized to dissolve over a selected treatment time period such as 10-15 minutes (or more). Each guard 32, 33 has a tab 44 that enables dislocation of the guard 32 or 33 from body 20 such as when an insert 13 is to be removed and body 20 is to be cleaned.

Figure 2:
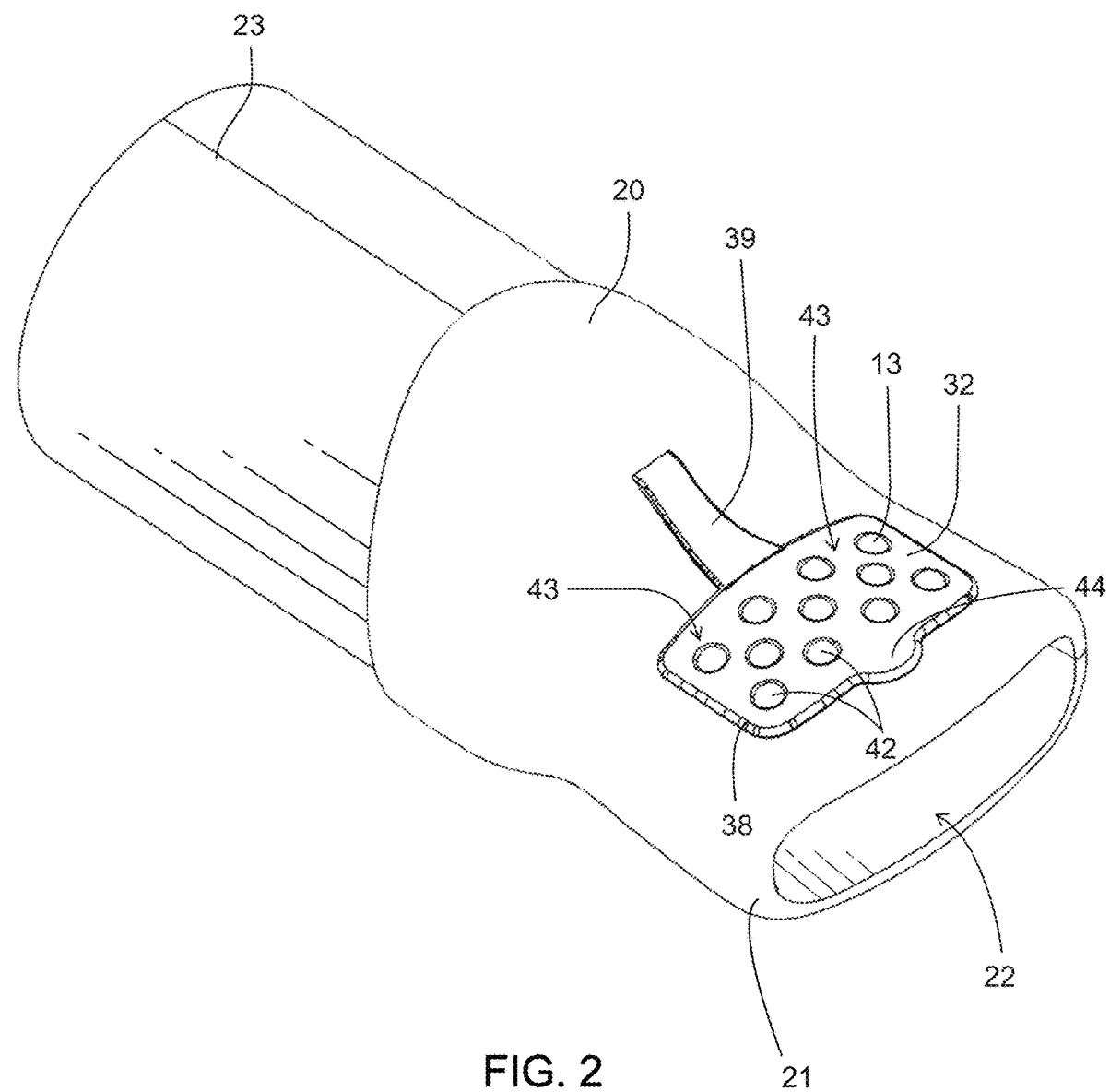
FIG. 2 is a perspective view of a preferred embodiment of the apparatus of the present disclosure with guard in closed position.
Figure 3:
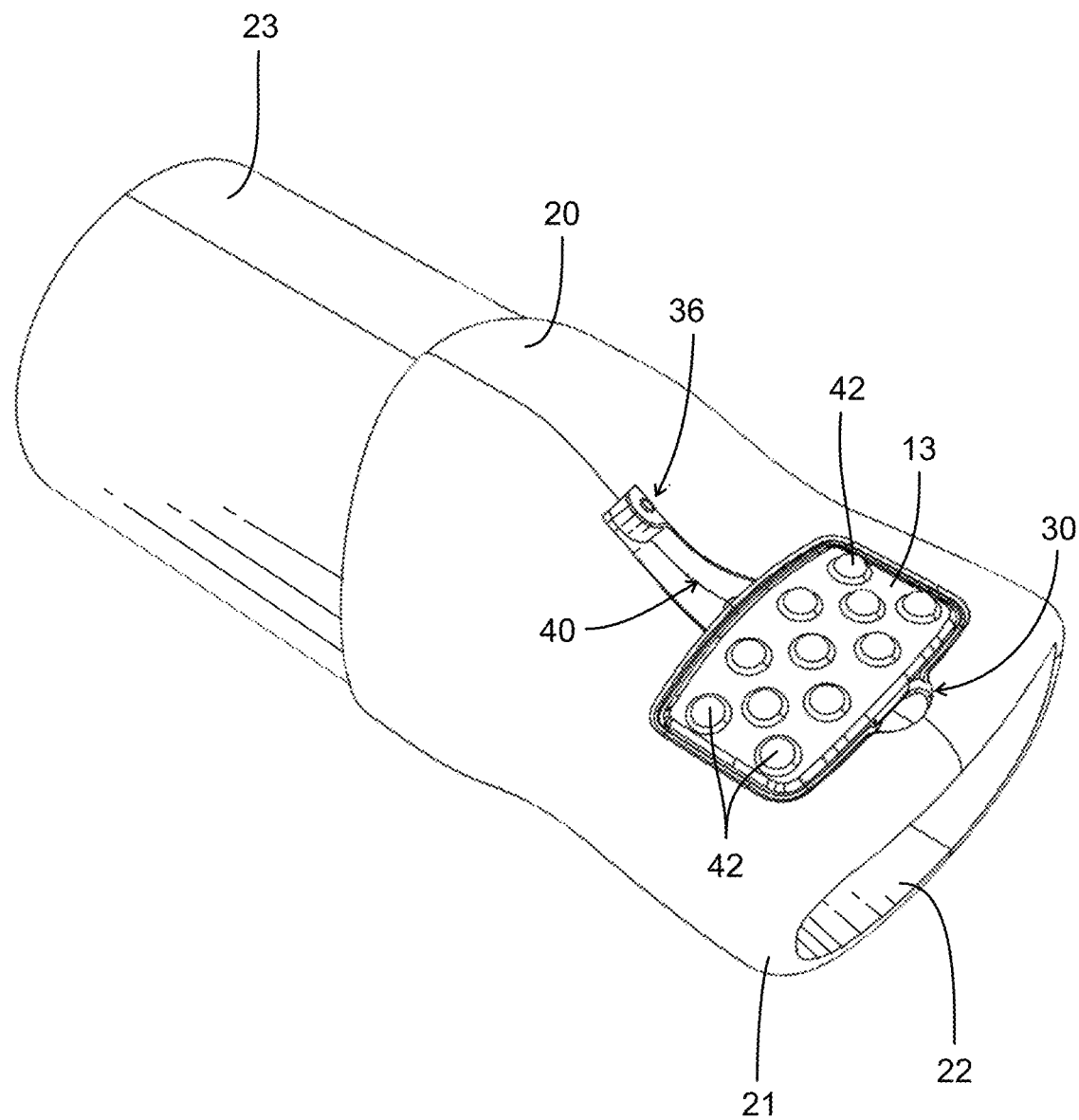
FIG. 3 is a perspective view of a preferred embodiment of the apparatus of the present disclosure with guard removed.
Figure 5:
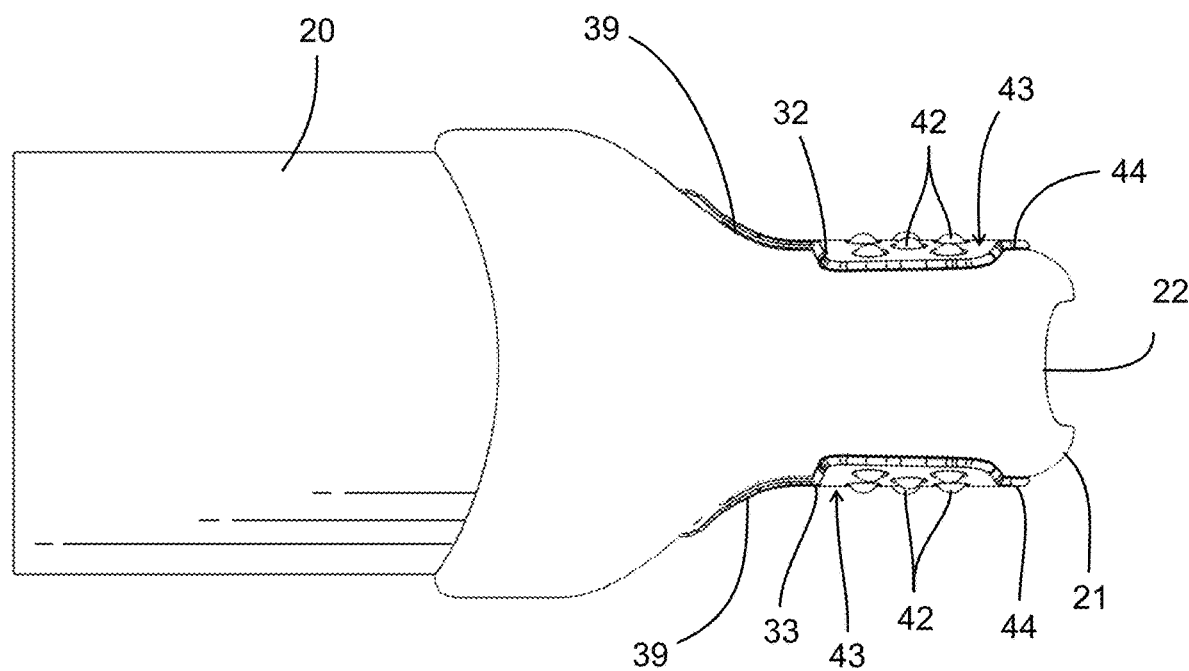
FIG. 5 is a side view of a preferred embodiment of the apparatus of the present disclosure with guard in closed position.
Figure 6:
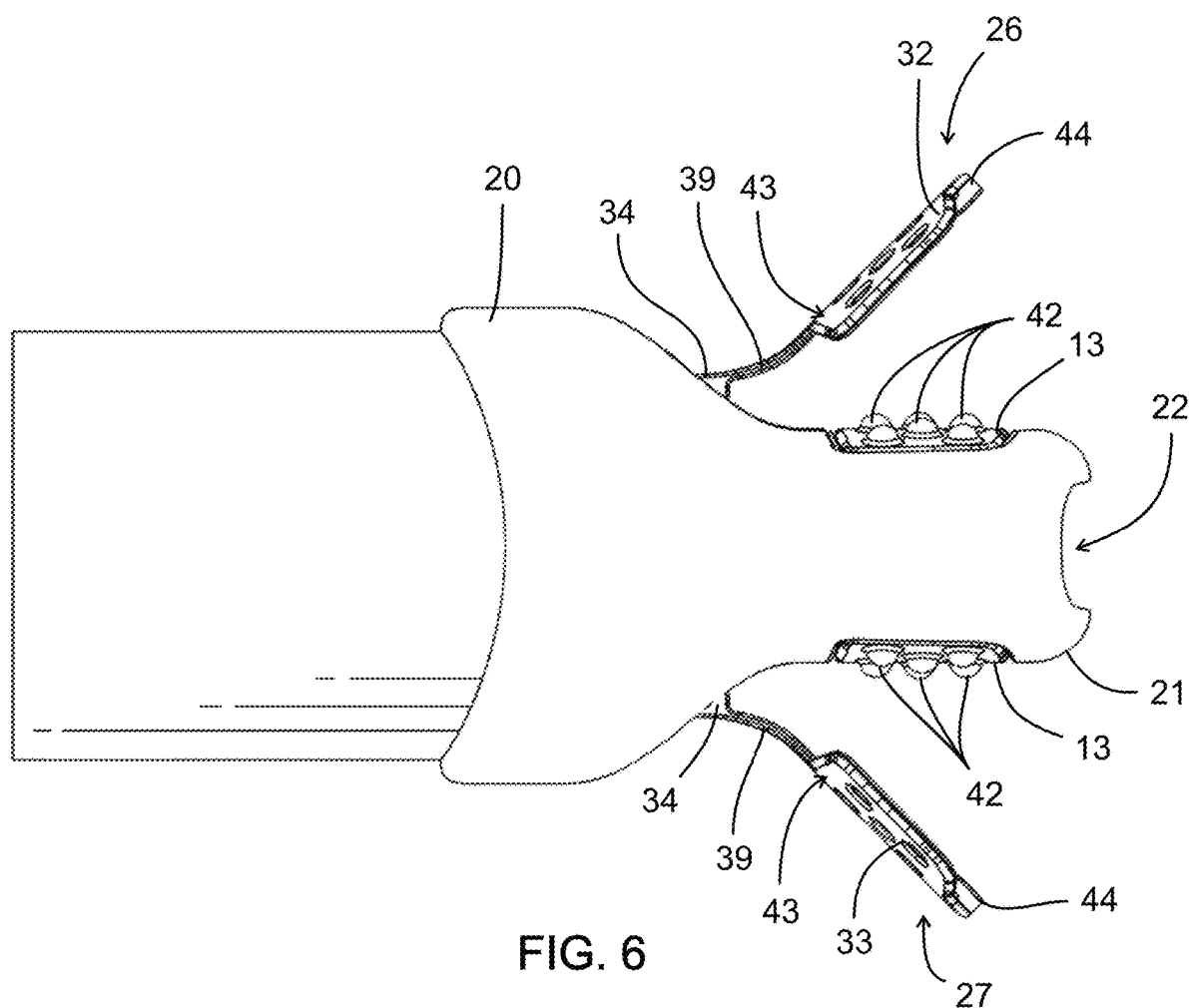
FIG. 6 is a side view of a preferred embodiment of the apparatus of the present disclosure with guards in open position.
Figure 7:
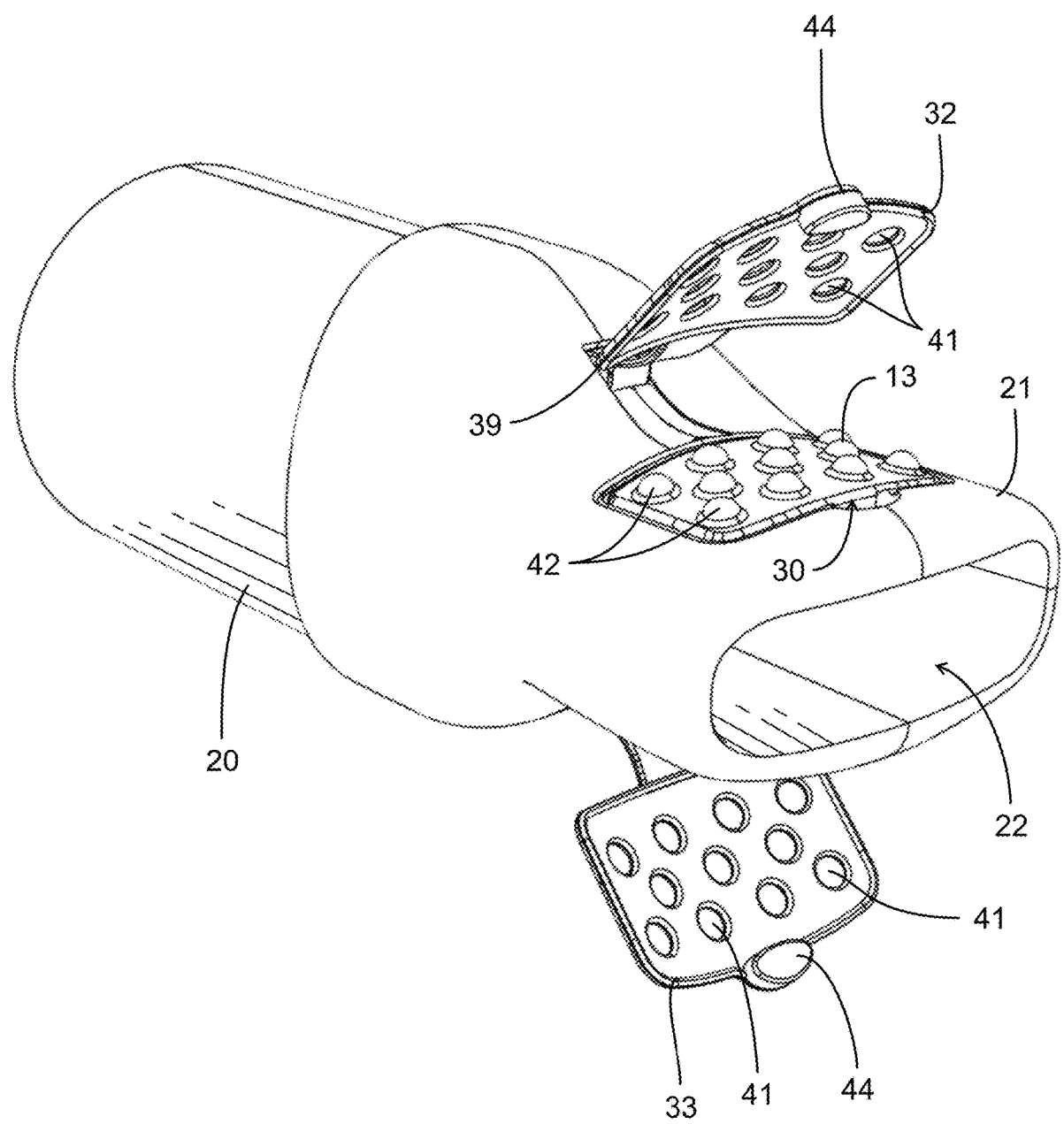
FIG. 7 is a perspective view of a preferred embodiment of the apparatus of the present disclosure with guards in an open position.
Figure 8:
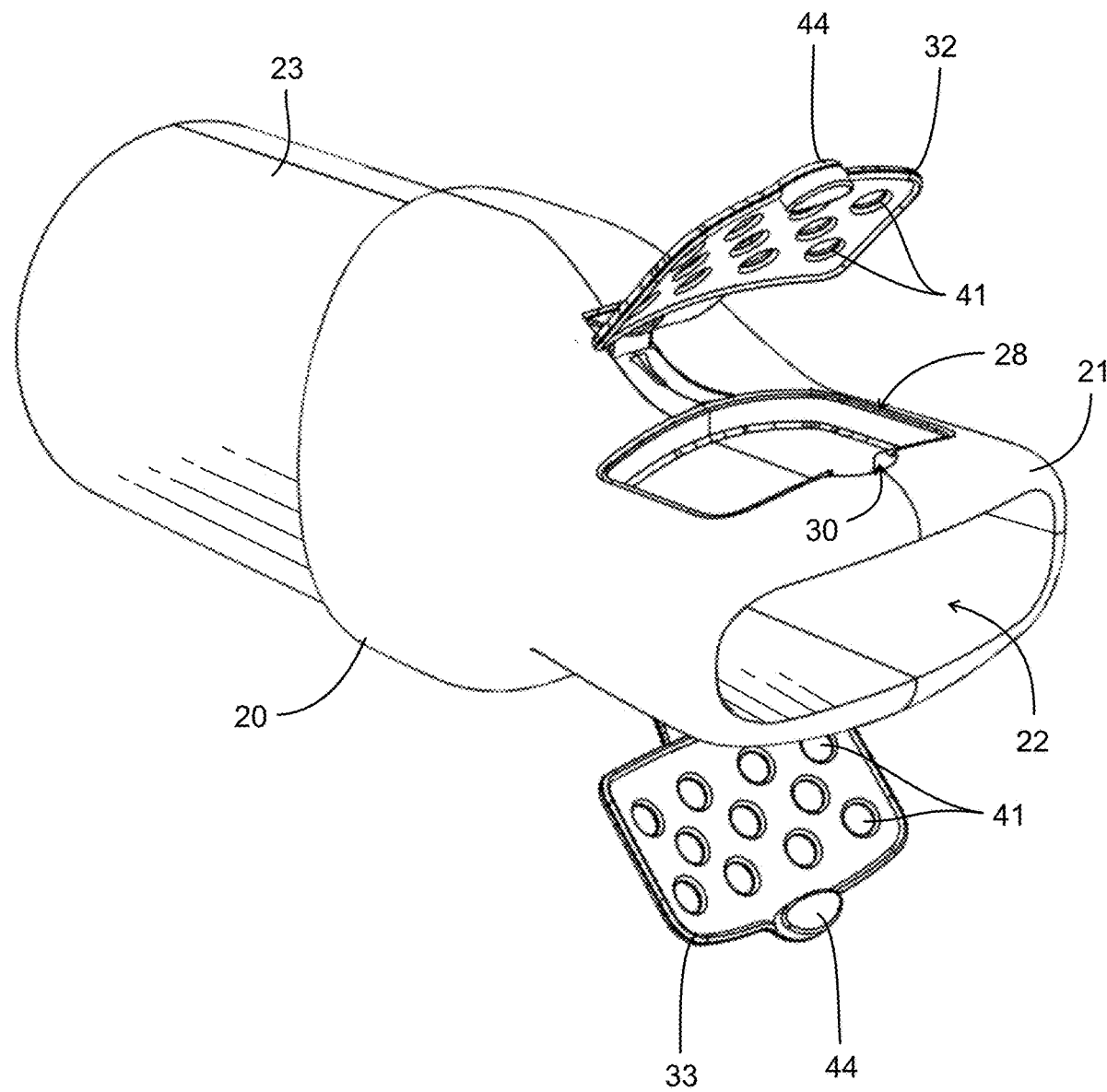
FIG. 8 is a perspective view of a preferred embodiment of the apparatus of the present disclosure with candy insert removed.
Figure 9:
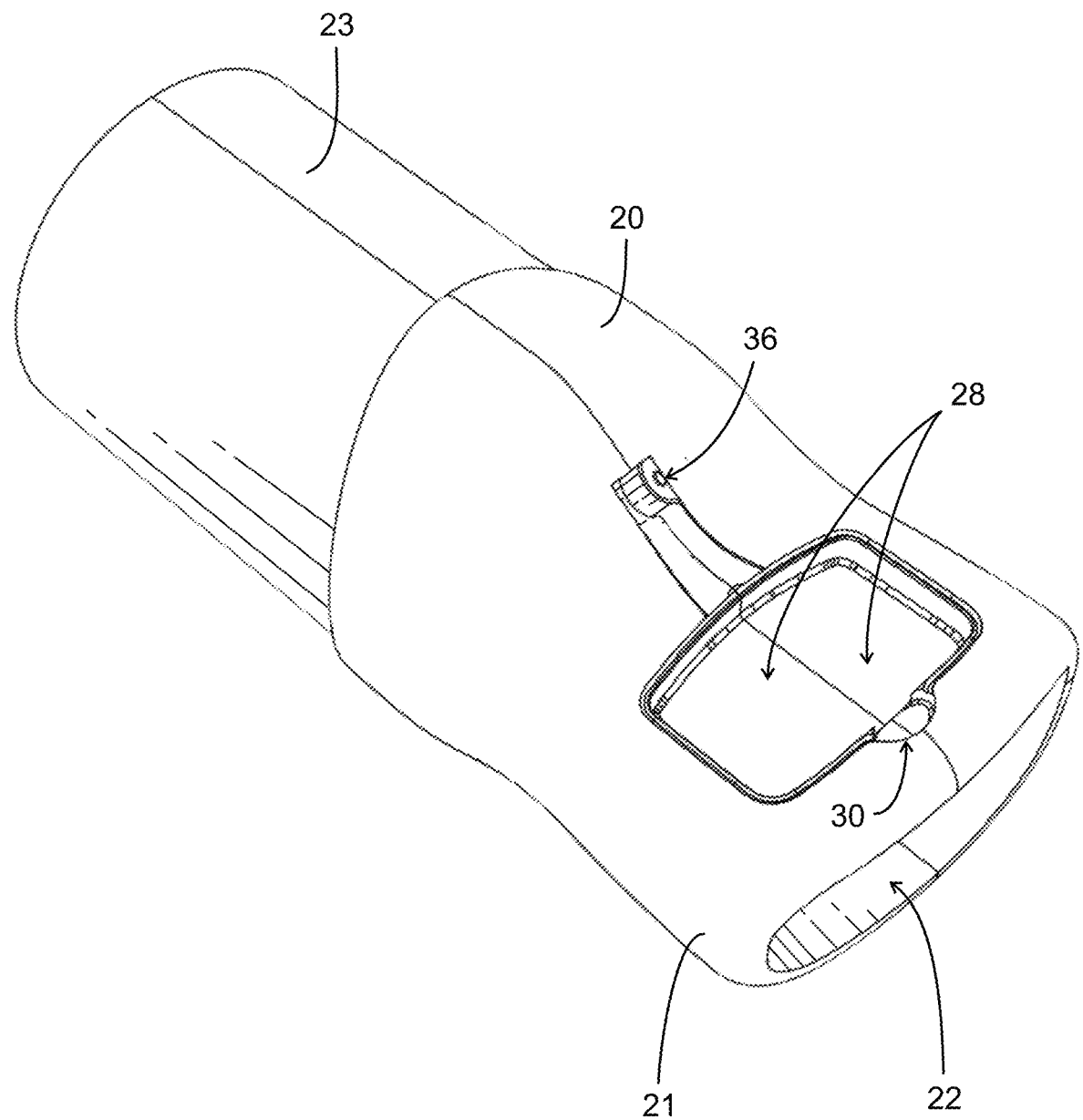
FIG. 9 is a perspective view of a preferred embodiment of the apparatus of the present disclosure with guard and candy insert removed.
Figure 10:
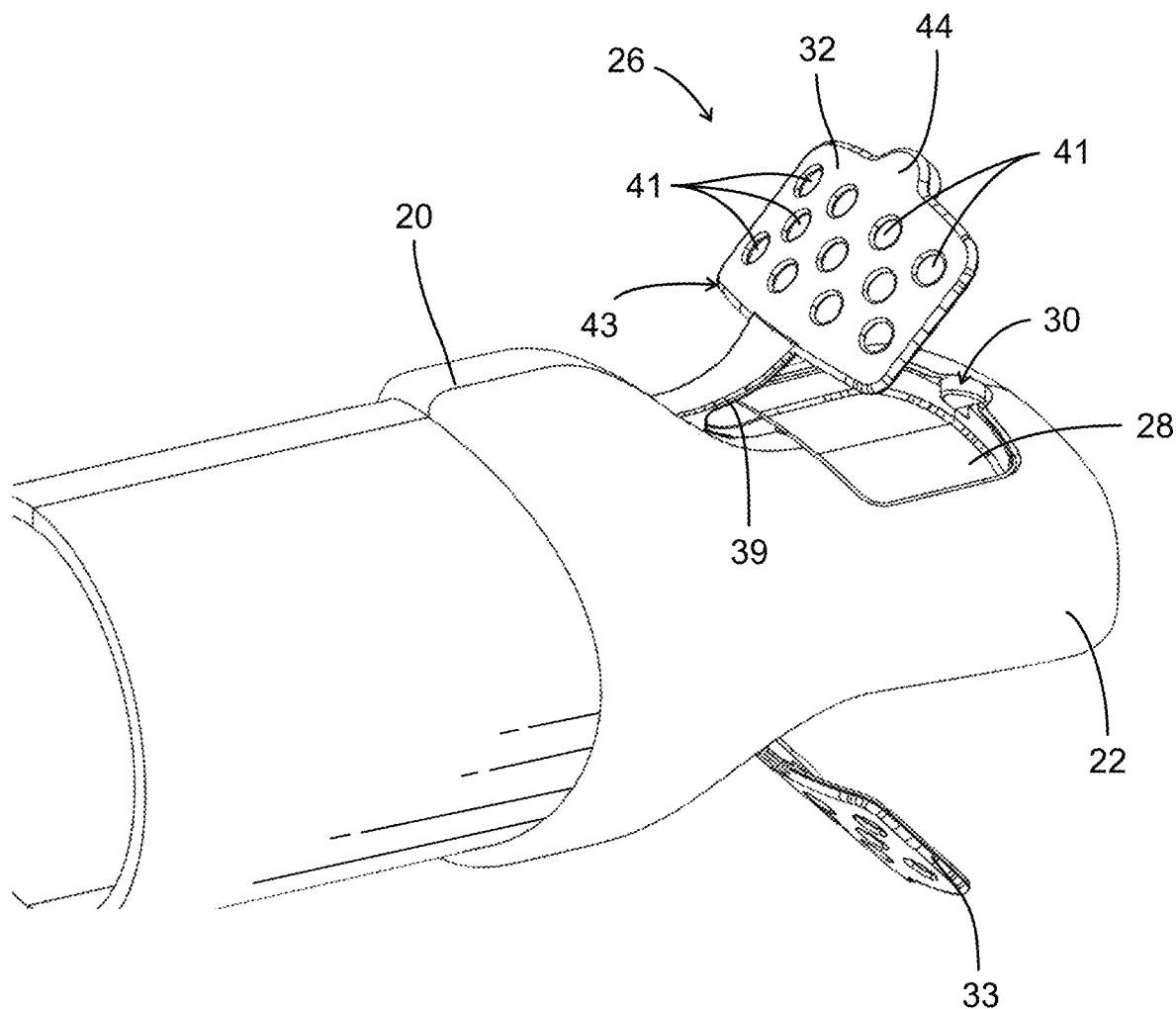
FIG. 10 is a perspective view of a preferred embodiment of the apparatus of the present disclosure with candy insert removed.
Figure 11:
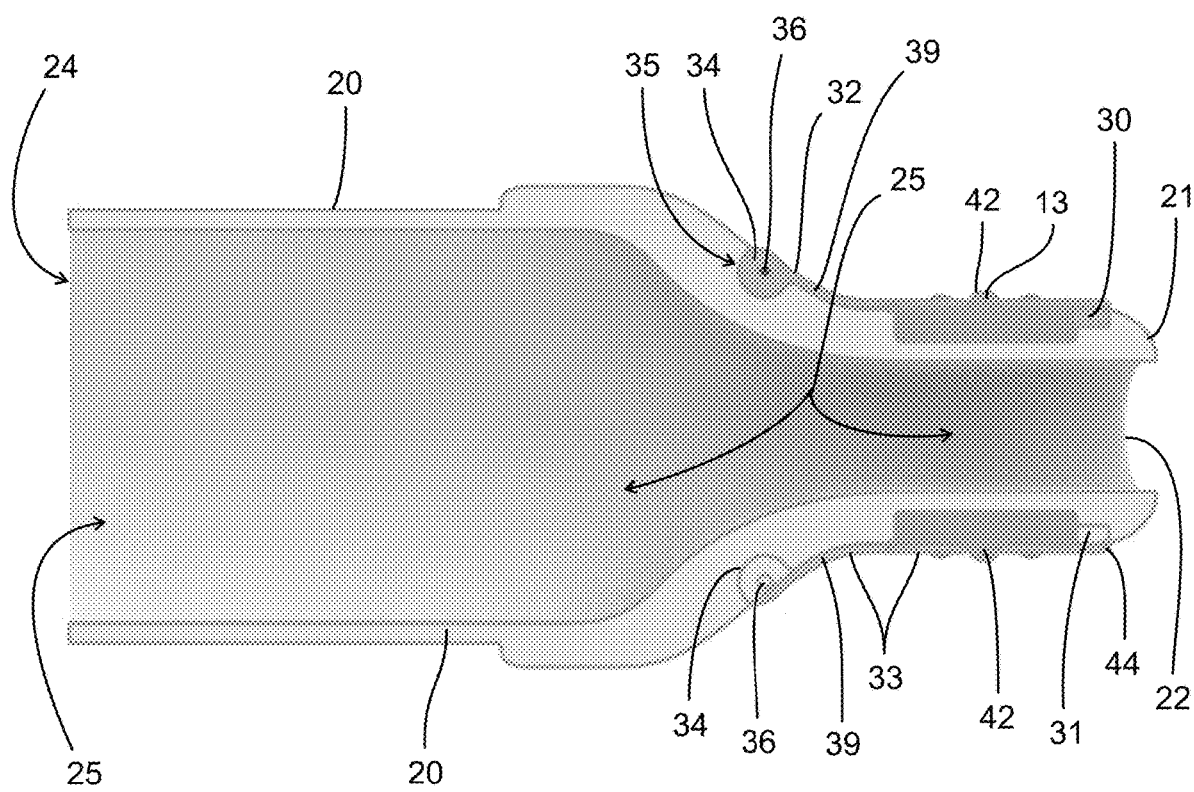
FIG. 11 is a sectional view of a preferred embodiment of the apparatus of the present disclosure.
Figure 12:
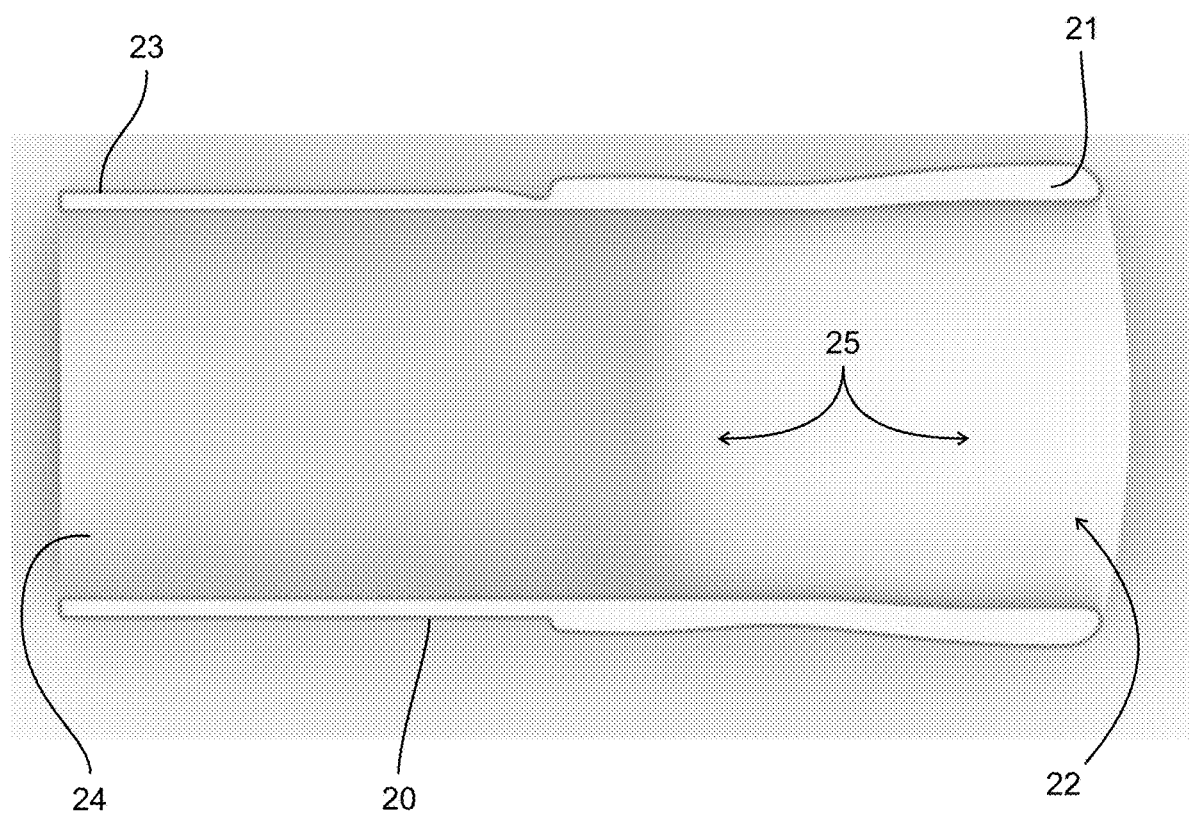
FIG. 12 is a partial sectional view of a preferred embodiment of the apparatus of the present disclosure.

Each tab 44 nests in a semicircular or arcuate recess 30 or 31. A user (parent or medical personnel) can remove the selected guard 32 or 33 thus pivoting arm or strap about pivot 36 to an open position (FIGS. 6-8, 10, and 16-17). The operational closed position is seen in FIGS. 2, 5 and 11.

The flavor attachment 13 is preferably sized and shaped to fit with a standard pediatric nebulizer cup or inhaler. For example, in some preferred embodiments, the attachment 13 is rectangular shaped having a length of approximately 16-17 mm and width of approximately 10-11 mm. Preferably, the rectangular attachment 13 can be curved to attach to the inhaler mouthpiece, causing the total height to be approximately 3.5-4.5 mm.

While the duration of treatment is typically interval of between about 1 and 20 minutes, in some children it could be hours, in which case an especially long-lasting candy or flavored substance could be used, or the candy or substance could be replaced as needed during the duration of treatment.

PARTS LIST

The following is a list of parts and materials suitable for use in the present device:
Parts Number Description
   10 respiratory therapy apparatus
   11 nebulizer/nebulizer cup
   12 mouthpiece 13 candy item/candy fitment/candy coating/candy layer/ flavor attachment
14 child
15 compressor
16 tubing section
20 mouthpiece
21 end portion
22 opening
23 end portion
24 opening
25 flow bore
26 guard assembly
27 guard assembly
28 recess, rectangular recess
29 recess, rectangular recess
30 semicircular recess
31 semicircular recess
32 upper guard
33 lower guard
34 hinge portion
35 hinge recess
36 pivot pin, pinned connection
37 pin opening
38 rectangular portion
39 strap/arm
40 recess
41 opening
42 projection/bump
43 outer surface
44 tab All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present disclosure is to be limited only by the following claims.

Many modifications and other embodiments of the invention will come to mind to one skilled in the art to which this invention pertains having the benefit of the teachings presented in the foregoing descriptions, and the associated drawings. Therefore, it is to be understood that the invention is not to be limited to the specific embodiments disclosed. Although specific terms are employed herein, they are used in a generic and descriptive sense only and not for purposes of limitation. As such, it is understood that versions of the present disclosure may come in different forms and embodiments. Additionally, it is understood that one of skill in the art would appreciate these various forms and embodiments as falling within the scope of the invention as disclosed herein.

What is claimed is:

1. A mouthpiece comprising:
   a body having an opening that enables transmission of airborne particles to a user through the opening, wherein the body has a recess on an exterior of the body;
   a consumable flavored attachment sized to fit within the recess, wherein the flavored attachment has one or more projecting portions; and
   a guard that retains the flavored attachment within the recess, wherein the guard has one or more open portions that enable the one or more projecting portions of the flavored attachment to extend through the one or more open portions of the guard so that the user tastes the flavored attachment when the user holds the mouthpiece in the user's mouth.

2. The mouthpiece of claim 1, wherein the flavored attachment is a hard candy.

3. The mouthpiece of claim 1, wherein at least the one or more projecting portions of the flavored attachment are designed to dissolve in the user's mouth when the user holds the mouthpiece in the user's mouth.

4. The mouthpiece of claim 3, wherein the one or more projecting portions of the flavored attachment are designed to dissolve over a time period that equates with a prescribed treatment duration of an inhaled pharmaceutical during which time the user retains the mouthpiece in the user's mouth.

5. The mouthpiece of claim 1, wherein the guard has a thickness and each of the one or more projecting portions has a height that is greater than the thickness of the guard.

6. The mouthpiece of claim 1, wherein the guard is movable between an open position and a closed position, wherein the flavored attachment is removable from the recess when the guard is in the open position, and wherein the flavored attachment is retained within the recess when the guard is in the closed position.

7. The mouthpiece of claim 6, wherein the guard is hingedly attached to the mouthpiece.

8. The mouthpiece of claim 1, wherein the one or more projecting portions of the flavored attachment are arranged in a pattern that corresponds to a pattern of the one or more open portions of the guard.

9. The mouthpiece of claim 8, wherein the one or more projecting portions of the flavored attachment are arranged in rows.

10. A mouthpiece comprising:
    a body having an opening that enables transmission of airborne particles to a user through the opening, wherein the body has an upper recess on an upper side of an exterior of the body and a lower recess on a lower side of the exterior of the body;
    a pair of consumable flavored attachments comprising an upper flavored attachment and a lower flavored attachment, wherein the upper flavored attachment is sized to fit within the upper recess, and the lower flavored attachment is sized to fit within the lower recess, wherein each of the flavored attachments has one or more projecting portions; and
    an upper guard and a lower guard, wherein the upper guard retains the upper flavored attachment within the upper recess, wherein the lower guard retains the lower flavored attachment within the lower recess, wherein the upper guard has one or more open portions that enable the one or more projecting portions of the upper flavored attachment to extend through the one or more open portions of the upper guard, and wherein the lower guard has one or more open portions that enable the one or more projecting portions of the lower flavored attachment to extend through the one or more open portions of the lower guard so that the user tastes the flavored attachments when the user holds the mouthpiece in the user's mouth,
    wherein each of the guards is movable between an open position and a closed position, wherein the upper and lower flavored attachments are removable from the upper and lower recesses, respectively, when the upper and lower guards are each in the open position, and wherein the upper and lower flavored attachments are retained within the upper and lower recesses, respectively, when the upper and lower guards are each in the closed position.

11. The mouthpiece of claim 10, wherein each of the flavored attachments is a hard candy.

12. The mouthpiece of claim 10, wherein at least the one or more projecting portions of each of the flavored attachments are designed to dissolve in the user's mouth when the user holds the mouthpiece in the user's mouth.

13. The mouthpiece of claim 12, wherein the one or more projecting portions of each of the flavored attachments are designed to dissolve over a time period that equates with a prescribed treatment duration of an inhaled pharmaceutical during which time the user retains the mouthpiece in the user's mouth.

14. The mouthpiece of claim 10, wherein the one or more projecting portions of each of the flavored attachments are arranged in a pattern that corresponds to a pattern of the one or more open portions of each respective one of the guards.

15. A method of using a mouthpiece, said method comprising the steps of:
- providing a mouthpiece comprising:
  - a body having an opening that enables transmission of airborne particles to a user through the opening, wherein the body has a recess on an exterior of the body,
  - a consumable flavored attachment sized to fit within the recess, wherein the flavored attachment has one or more projecting portions, and
  - a guard that retains the flavored attachment within the recess, wherein the guard has one or more open portions that enable the one or more projecting portions of the flavored attachment to extend through the one or more open portions of the guard so that the user tastes the flavored attachment when the user holds the mouthpiece in the user's mouth;
- positioning the flavored attachment within the recess;
- placing the mouthpiece within the user's mouth so that the flavored attachment is disposed within the user's mouth; and
- the user inhaling the atomized particles through the opening while tasting the flavored attachment.

16. The method of claim 15, wherein the flavored attachment is a hard candy.

17. The method of claim 15, wherein at least the one or more projecting portions of the flavored attachment are designed to dissolve in the user's mouth when the user holds the mouthpiece in the user's mouth, wherein the step of the user tasting the flavored attachment is facilitated by the dissolving of the one or more projecting portions of the flavored attachment.

18. The method of claim 17, wherein the one or more projecting portions of the flavored attachment are designed to dissolve over a time period that equates with a prescribed treatment duration of an inhaled pharmaceutical during which time the user retains the mouthpiece in the user's mouth.

19. The method of claim 15, wherein the guard is movable between an open position and a closed position, wherein the flavored attachment is removable from the recess when the guard is in the open position, wherein the flavored attachment is retained within the recess when the guard is in the closed position, and wherein the step of positioning the flavored attachment within the recess comprises moving the guard to the open position, placing the flavored attachment within the recess, and then moving the guard to the closed position to retain the flavored attachment within the recess.

20. The method of claim 15, wherein the guard has a thickness and each of the one or more projecting portions has a height that is greater than the thickness of the guard.

* * * * *